(12) United States Patent
Kudryavtsev et al.

(10) Patent No.: US 9,695,111 B2
(45) Date of Patent: Jul. 4, 2017

(54) METHOD OF PRODUCING SOLUBLE SILICATES WITH ORGANIC CATIONS

(71) Applicants: POLYMATE, LTD., Migdal Ha'Emeq (IL); NANOTECH INDUSTRIES, INC., Daly City, CA (US)

(72) Inventors: Pavel Kudryavtsev, Bat Yam (IL); Oleg Figovsky, Haifa (IL)

(73) Assignees: POLYMATE, LTD., Migdal Ha'Emeq (IL); NANOTECH INDUSTRIES, INC., Daly City, CA (US)

( * ) Notice: Subject to any disclaimer, the term of this patent is extended or adjusted under 35 U.S.C. 154(b) by 0 days.

(21) Appl. No.: 14/860,708

(22) Filed: Sep. 22, 2015

(65) Prior Publication Data

US 2017/0081274 A1    Mar. 23, 2017

(51) Int. Cl.
C07C 211/63    (2006.01)
C07C 211/06    (2006.01)
C07D 213/74    (2006.01)
C07D 487/04    (2006.01)
C07D 211/06    (2006.01)
C07C 211/58    (2006.01)

(52) U.S. Cl.
CPC .......... *C07C 211/63* (2013.01); *C07C 211/06* (2013.01); *C07C 211/58* (2013.01); *C07D 211/06* (2013.01); *C07D 213/74* (2013.01); *C07D 487/04* (2013.01)

(58) Field of Classification Search
CPC ... C07C 211/63; C07C 211/58; C07C 211/06; C07D 487/04; C07D 213/74
USPC .................................................. 556/400, 413
See application file for complete search history.

(56) References Cited

U.S. PATENT DOCUMENTS

| | | |
|---|---|---|
| 2,689,245 A | 9/1954 | Merrill |
| 3,239,521 A | 3/1966 | Weldes |
| 3,326,910 A | 6/1967 | Weldes |
| 4,169,735 A | 10/1979 | Bobersky |
| 4,487,712 A | 12/1984 | Wilson et al. |

FOREIGN PATENT DOCUMENTS

| | | |
|---|---|---|
| GB | 709634 | 6/1954 |
| KR | 20150001529 | 1/2015 |

*Primary Examiner* — Porfirio Nazario Gonzalez
(74) *Attorney, Agent, or Firm* — TransPacific Law Group; Pavel I. Pogodin, Esq.

(57) ABSTRACT

Proposed is a method of producing soluble silicates with organic cations at a given silicate modulus in the range of 1.5 to 20. The method consists of the reacting liquid suspension of a silica sol with the aqueous solution of a strong organic base. The silicate modulus is a molar ratio of $SiO_2:M_2O$, wherein M is an organic alkali cation. The aqueous solution of a strong organic base has a constant of base dissociation $pK_b$ equal to or greater than 4. If necessary, the soluble silicates with organic cations are obtained in a powdered form by evaporating the solution of the soluble silicates under vacuum below 4.2 kPa and at a temperature in the range of 20 to 30° C. and the product of evaporation are then dried by spraying.

21 Claims, 3 Drawing Sheets

METHOD OF PRODUCING SOLUBLE SILICATES WITH ORGANIC CATIONS

BACKGROUND OF THE INVENTION

Field of the Invention

This invention relates generally to the production and use of soluble organic silicates with organic cations without alkali metals and, in particular, to a process for rapid and effective production of various silicates with strong organic bases.

Description of the Related Art

Water-soluble alkali metal silicates are unique components that find use in the following practical applications:

(1) refractory cements and fast setting concretes;
(2) refractory inorganic coatings and environmentally stable coatings;
(3) various adhesives;
(4) components of heat-resistant paints;
(5) binders for precision casting;
(6) precursors used in the synthesis of silica-sols by an ion-exchange method and in the manufacture of silica gels;
(7) compositions with sols for the preparation of mesoporous adsorbents;
(8) hybrid composites;
(9) detergents and cleaning compositions.

However, for some applications, the water-soluble alkali metal silicates are disadvantageous since one of their components is an alkali metal the presence of which in undesirable. Therefore, finding of soluble silicates which are free of alkali metal-containing components and could be used in various industrial applications has long been a goal of the industry. For example, the presence of alkali metal compounds in refractory cements lowers the softening point of such cements due to the formation of low-melting components. Attempts to overcome this problem have been made by increasing the silica modulus of the soluble silicate or by replacing sodium or potassium by the lithium. In this case, however, some amount of alkali metal always remains, even after thorough washing and acidizing. Furthermore, at high silica moduli and high concentrations, the alkali metal silicate solutions lead to rapid increase in viscosity.

Artificial silicate stones can be prepared on the basis of a conventional cement technology by using, for example, blast furnace slag mixed with pulverized quartz, quartz sand, or the like. When such a mixture is combined with liquid glass as a binder, it quickly hardens and acquires a number of valuable properties. When used as a filler, quartz sand (milled or unmilled) in a mixture with a liquid glass (M=2.5-2.6), after molding, drying and calcination, allows obtaining products in the form of tiles, blocks, or bricks. Such a process also leads to increase in the silicate modulus of the system.

In addition to alkali metal hydroxides, there exist many other strong bases, mainly organic, the cations of which form with silicate anions only poorly soluble compounds. High levels of silicate can be obtained directly by dissolving silica in aqueous solutions of $NR_4OH$, wherein R designates aliphatic radicals (alkyls) or aromatic radicals (aryls) or their substituted derivatives.

On the other hand, solutions of quaternary ammonium silicate differ from liquid mineral glasses by the following properties:

low viscosity of solutions at equal concentrations of $SiO_2$;
higher stability of solutions against gelation;
high affinity of silicate solutions with organic bases to water-soluble organic substances such as alcohols, ketones, etc. (especially, when these compounds are used as binders in processes for obtaining inorganic composite materials).

Products of hardening of such binders are corresponding crystalline and amorphous quaternary ammonium hydrous silicates, e.g., tetraethyl ammonium hydrous silicate $[(C_2H_5)4N]_2O.7SiO_2.17.2N_2O$; tetrabutyammonium hydrous silicate $[(C_4H_9)4N]_2O.6SiO_2.14.3N_2O$; hydrous tetraetanolammonium hydrous silicate $[(C_2H_4OH)4N]_2O.0.5$ to $20SiO_2.1$ to $99N_2O$, and others.

Use of a quaternary ammonium silicate is based primarily on the use of a silica component. The role of the organic auxiliary base is to impart some technological properties to the system used.

Application of alkali silicate binders is similar to the use of liquid glass. However, a silicate binder has a significant advantage over the liquid glass in cases where there are restrictions on the content of alkali oxides such as $Na_2O$ and $K_2O$ in the material. An organic base thermally dissociates at relatively low temperatures (200 to 300° C.), but most of the binding properties of the material (50-70%) are preserved. At temperatures above 300° C. silica forms a solid film. The greatest interest is the use of such binders in preparation of protective and decorative silicate coatings, as well as temperature-resistant coatings.

The traditional area for use of a quaternary ammonium silicate is the production of anticorrosion zinc-filled silicate paints and varnishes. Prospective application of a quaternary ammonium silicate is their use as a binder for casting, molding, core mixtures, and as heat-resistant and fire-resistant composite materials. Quaternary ammonium silicates also find application in several other areas of technology associated with water-soluble silicates. An example of high-temperature coatings that contain quaternary ammonium silicate includes mold dressing for casting ferrous and non-ferrous metals.

U.S. Pat. No. 3,239,521 discloses obtaining of amorphous compositions having a general formula of an oxide with continuously adjustable ratios of compound components:

$$X(N_nR_p^s)_2O.YSiO_2.ZH_2O,$$

where:

N is a nitrogen atom;

n is a number not higher than 10 and preferably smaller than 5;

X, Y, Z are values which describe relative quantities of compound components, where X is 1, Y is mainly in the range of 0.5 to 20, and Z is in the range of 0 to 99, and wherein each N atom is linked to up to four R groups, where R represents alkyl radicals containing about 1 to 20 carbon atoms, wherein at least two of the alkyl radicals are w-hydroxyalkyl groups (two or more of which comprise ethanol groups or other derivatives of the ethanol groups);

p is at least 4, which indicates the number of identical groups R; and s is an even number from 1 to p that indicates the number of groups R of different types.

The aforementioned materials are obtained by various methods, which include, e.g., the following:

(a) removing ions of alkali metals from the hydroxylated quaternary ammonium silicates with an alkali metal by using a suitable ion exchange resin;

(b) dissolving silica in hydroxylated organic quaternary ammonium bases;

(c) dissolving silica in sodium silicate of tetraetanolammonium; or (d) reacting ammonia or amine with finally disintegrated silicon oxide hydrate or colloidal silica sol.

All these processes are difficult to implement and involve the use of ethylene oxide. Furthermore, they allow obtaining only of ethanolamine derivatives and their silicates and require additional purification of the products obtained from the alkali metal salts.

Known in the art are also methods for preparing quaternary ammonium silicates by dissolving finely disintegrated quartz or silica gel in solutions of quaternary ammonium bases (GB Patent No. 709,634). However, such processes of synthesis of quaternary ammonium silicates take long time and proceed for several tens of hours. Furthermore, they do not proceed to the completion and require removal of non-reacted silicon oxide particles from the reaction medium. There is a significant difference between silica particles prepared in aqueous media and silica particles obtained at high temperature, e.g., by a pyrogenic method, when immediately after preparation the particles are subjected to dispersion in water. Some of the non-hydroxylated surface of pyrogenic silica may for some time be kept in an unchanged form. Therefore, only a part of the surface will be covered by SiOH groups which can undergo dissociation and can be ionized. This factor also contributes to delaying the dissolution of silicon compounds in alkaline solutions.

It is known that small silica particles are soluble in aqueous solutions of weak bases with dissociation constants $pK_b$ in the range of 4 to 5, but normally such processes proceed very slow (see, e.g., U.S. Pat. No. 2,689,245, which discloses the preparation of several water-soluble quaternary ammonium silicates by adding particulate silica gel to a basic solution).

According to another method suitable for preparing organic silicates of the above-described type, $(HOC_2H_4)_4N^+ OH^-$ is added to the silicate sodium solution having a 3.75:1.0 ratio of $SiO_2$ to $Na_2O$ with subsequent removal of sodium by ion exchange with sodium ions $(HOC_2H_4)_4N^+$ on a cation-exchange resin.

The mixture first forms a gel, but then turns into a viscous solution. Another embodiment of the method is the preparation of a dilute solution of ethanolamine and silica in a similar way with the subsequent formation of a quaternary ammonium salt by reaction with ethylene oxide (U.S. Pat. No. 3,326,910). Also known is a method for preparing silicates of diethanolammonium, morpholine and corresponding related salts (U.S. Pat. No. 3,239,521). It is relatively difficult to selectively remove ions of alkali metals from a mixture of organic cations and alkali metal ions on the cation exchange resin. This may lead to clogging of the ion-exchange column with the gel formed and thus to increasing of the hydrodynamic resistance of the column. Such a situation may lead to large losses of silicon compounds and to a considerable reduction in the yield of the finished product.

SUMMARY OF THE INVENTION

This invention relates generally to soluble organic silicates with organic cations without alkaline metals. In particular, the invention relates to a rapid and highly productive method for obtaining soluble organic silicates of various strong bases.

The invention offers a method for producing soluble silicates with organic cations at a molar ratio $SiO_2:M_2O$ (where M is an organic alkaline cation) in the range of 1.5 to 20.0, preferably in the range of 1.5 to 4.0. The method consists of the following steps:

a) preparing an aqueous suspension of a finely divided silica in the form of silica sol obtained by removing ions of an alkali metal from a solution of alkali metal silicate by an ion-exchange method;

b) interacting the obtained suspension with an aqueous solution of a strong organic base; and c) obtaining a soluble silicate with organic cations having a given molar ratio of $SiO_2:M_2O$.

If necessary to obtain the target product in the form of a powder, the obtained solution is subjected to evaporation with subsequent spray drying.

The silica sol is used with particles having dimensions in the range of 2 to 20 nm, preferably with concentration of particles in the range of 1 to 100 g/l.

The interaction of the obtained suspension with the aqueous solution of a strong organic base is carried out at a molar ratio of $SiO_2:M_2O$ in the range of from 1.5 to 20.0, preferably 1.5 to 4.0.

The strong organic base used in the process may comprise an organic quaternary ammonium hydroxide of the following general formula:

$$R_1R_2R_3R_4NOH,$$

where $R_1$, $R_2$, $R_3$, , n=1 to 5, m=3 to 13.

Additional aspects related to the invention will be set forth in part in the description which follows, and in part will be obvious from the description, or may be learned by practice of the invention. Aspects of the invention may be realized and attained by means of the elements and combinations of various elements and aspects particularly pointed out in the following detailed description and the appended claims.

It is to be understood that both the foregoing and the following descriptions are exemplary and explanatory only and are not intended to limit the claimed invention or application thereof in any manner whatsoever.

BRIEF DESCRIPTION OF THE DRAWINGS

The accompanying drawings, which are incorporated in and constitute a part of this specification exemplify the embodiments of the present invention and, together with the description, serve to explain and illustrate principles of the inventive technique. Specifically.

DETAILED DESCRIPTION

In the following detailed description, reference will be made to the accompanying drawing(s), in which identical functional elements are designated with like numerals. The aforementioned accompanying drawings show by way of illustration, and not by way of limitation, specific embodiments and implementations consistent with principles of the present invention. These implementations are described in sufficient detail to enable those skilled in the art to practice the invention and it is to be understood that other implementations may be utilized and that structural changes and/or substitutions of various components may be made without departing from the scope and spirit of present invention. The following detailed description is, therefore, not to be construed in a limited sense.

An objective of the present invention is to develop a process for the preparation of various silicates with strong organic bases, accelerate their production, and increase the output of the target products.

The essence of the proposed method consists of using a ready-made aqueous suspension of finely divided silica. Such an aqueous dispersion can be obtained from a silica sol, which, in turn, is prepared by removing alkali metal ions from the solution of an alkali metal silicate by ion exchange of alkali metal ions for hydrogen ions in the strongly acidic cation exchanger. The resulting suspension is reacted with an aqueous solution of a strong organic base, if necessary, with evaporation of the obtained solutions or spraying them for obtaining a product in the form of a dry powder.

Most finely divided silicas are in the form of colloidal particles in silica sol solutions. In such systems, the silica is in a hydrated form, in an active form, and in alkaline media. In the last-mentioned case, at all it is in equilibrium with some amount of monomers present in the solution. The rate of dissolution in an alkaline medium depends on the size of the primary particles and normally is sufficiently high.

Figure 1:
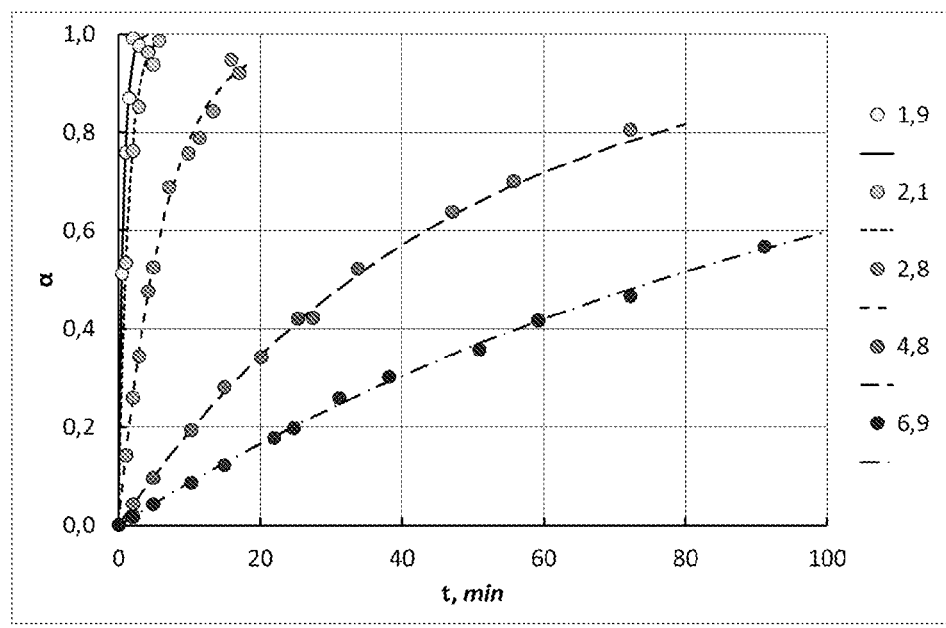
FIG. 1 is a graph that shows temporal variation of degree of transition of silica oxide into monomer forms during interaction of silica sols having various sizes of particles with solutions of tetraethylammonium at pH 9.5.

FIG. 1 shows the kinetic curves of dissolution of silica sol particles in a solution of tetraethylammonium hydroxide depending on the size of the primary particles. It is seen from this drawing that for silica sol particles in the range of 1.9 to 7 nm, a substantially complete dissolution of the silica particles with transition in monomeric form is achieved within a range of 5 minutes to 3 hours.

Figure 2:
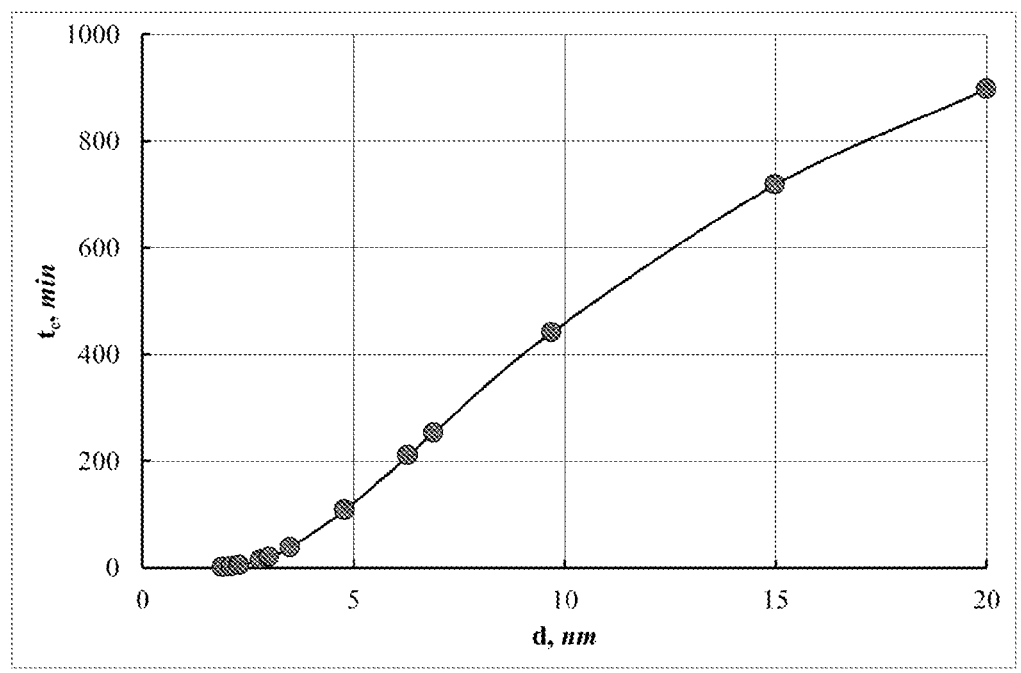
FIG. 2 is a graph that shows time needed to compete dissolving of colloidal particles of silica depending on the particle size of silica gel. The conversion time is time at which the degree of conversion a reaches 90%.

FIG. 2 is presented for better understanding a general nature of the process, which is dissolution of the colloidal particles in the silica sol solutions of strong organic bases. This drawing shows the time required to complete the dissolution of the colloidal silica particles depending on the particle size of silica sol. It is assumed that the time of conversion is the time passed until degree of conversion equal to α=90% is reached. It can be seen from the data presented in FIGS. 1 and 2 that the time technologically convenient for the process should not exceed 300 minutes. Therefore, for carrying out the process it is desirable to use a silica sol with the particle size not exceeding 7 to 8 nm. The lower limit for the size of particles of the used silica sol is 1 to 1.2 nm since simple synthesis practically does not allow obtaining particles of a size smaller than to 1 to 1.2 nm, and directly after the synthesis these particles rather quickly gain size, and even after brief storage reach the size greater than 1.5 nm.

Figure 3:
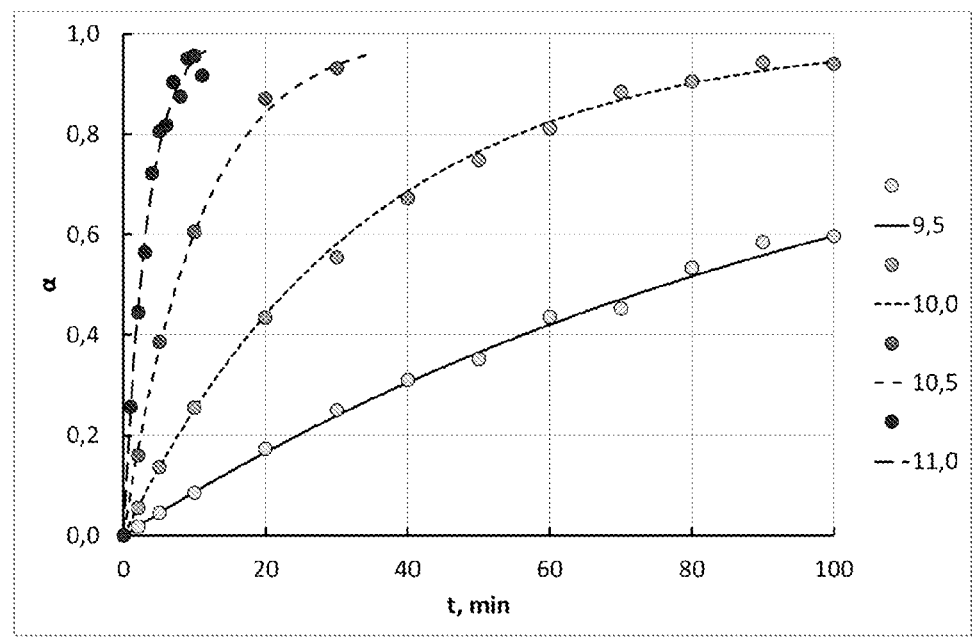
FIG. 3 is a graph that shows temporal variation of degree of transition of silica oxide into monomer forms during interaction of silica sols having the particle size of 6.9 nm with solutions of tetraethyl ammonia at different values of pH.

FIG. 3 shows the kinetic curves of dissolution of silica sol particles with the primary particle dimension of 6.9 nm in a solution of tetraethylammonium hydroxide depending on the value of the solution pH. It can be seen from this drawing that at a pH greater than 10 the silica gel particles of 6.9 nm can be almost complete dissolved with transition to a monomeric form and, depending on the size of the primary particles, such a transition is reached during the time in range from 5 minutes to 3 hours. Thus, an acceptable pH range is between 9 and 11. At pH less than 9, the dissolution process slows down dramatically, and the time needed for implementation of the process exceeds reasonable limits. On the other hand, pH greater than 11 leads to a significant consumption of reagents, in particular of fairly expensive compounds such as quaternary ammonium bases and other strong organic bases.

Figure 4:
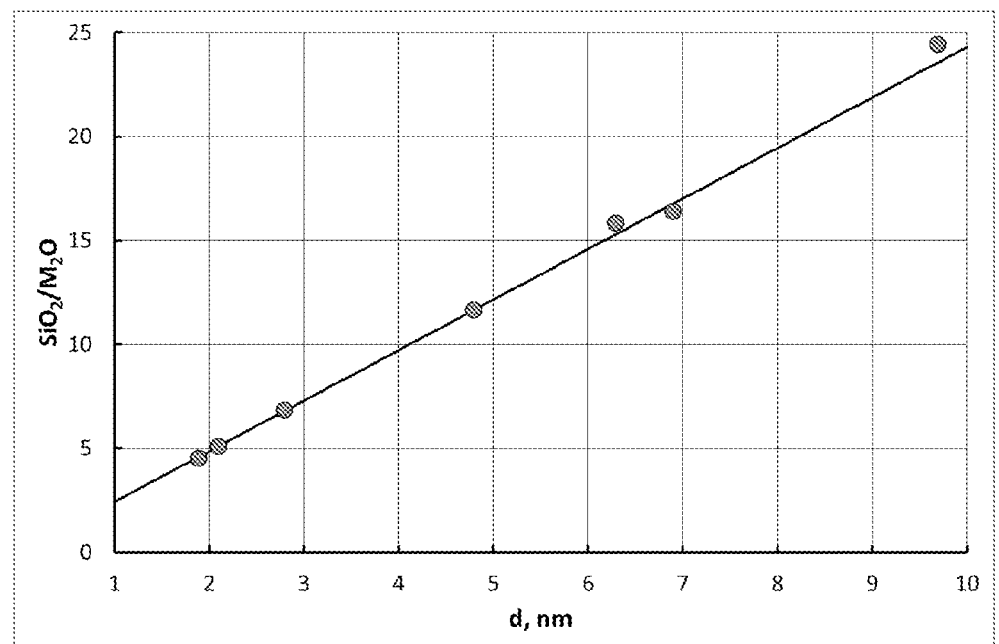
FIG. 4 is a graph that shows limit values of $SiO_2:M_2O$ silica modulus which can be obtained using silica sol neutralized by an organic base to pH 9.

In interaction of silica sols with strong organic bases, stabilization of sol can only be achieved by recharging its surface. For this purpose, it is sufficient to bring the pH to 9. In these conditions it is possible to obtain stable silicate systems with high silica modulus of $SiO_2:M_2O$. In this case, the magnitude of the resulting silicate modulus depends only on the diameter of the sol particles. Such a relationship is shown in FIG. 4. In fact, FIG. 4 is a state diagram of silicate systems with strong organic bases. The field of this diagram, which lies between the applied line and axis d (nm), corresponds to the region where stable colloidal polymeric and monomeric silicate systems may exist. Above this line, the corresponding silicate systems are subject to fairly rapid coagulation and gelation. Thus, for silica sol with the recommended limit particle size d of 7 to 8 nm, the limit for the theoretically possible silicate modulus of $SiO_2:M_2O$ will be in the range of 17 to 19.

As is known, soluble alkaline silicate systems are extensive and are classified according to the following criteria (The Chemistry of Silica, Raph K. Iler, John Wiley and Sons, New York, 1979):

(a) by a degree of polymerization (l) of silica, i.e., by an average number of silicon atoms that form during polymerization a continuous system of siloxane bonds $\equiv$Si—O—Si$\equiv$; polymerization of silica is accompanied by increase in its molecular weight (M), and at high degrees of polymerization, by increase in the size (d) of colloidal silica particles; at a certain degree of polymerization (l), colloidal silica appears in alkali silicate systems as a sol and as a highly hydrated silica:

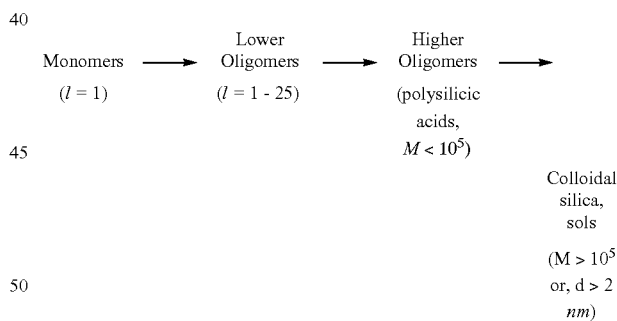

(b) by chemical composition in the course of increase in alkalinity, characterized by a molar ratio of $SiO_2/M_2O$ (silicate modulus n); in the case of alkali silicate systems, such systems form a row corresponding to the above four forms of silica:

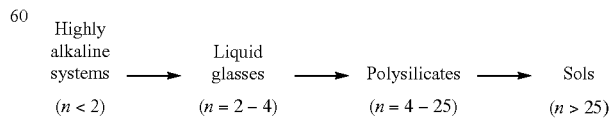

Thus, by analogy with silicate liquid glasses, for silicates of strong organic bases, optimal values of silica modulus of $SiO_2:M_2O$ is in the range of 2 to 4. For certain special cases, it can be brought to $SiO_2:M_2O$ in the range of 17 to 19, and even higher values. However, such systems are difficult to obtain, and they may be sufficiently unstable. The silica modulus $SiO_2:M_2O$ cannot have a value less than 2. Otherwise conventional molecular silicates, which do not possess binding properties, are formed.

In this process it is possible to use any type of strong organic bases. Since silica dissolves completely at pH 10.7 to 11.0 and even at high pH values, it is possible to prepare silicates of organic bases having dissociation constants $pK_b$ less than 3. The resulting compounds obtained in accordance with the aforementioned patent also will have a predetermined amount of silica modulus expressed by analogy with the silicate modulus of alkali metals in the form of $SiO_2:(NR_4)_2O$.

The most common method of producing hydrosols, in particular silicon oxide, is the method of ion exchange. In the present application the liquid glass solution with a content of 3 to 6% of $SiO_2$ was passed through a cation bed in the H form. In the process of the exchange, the sodium ions remain in the resin. As a result, the product that leaves the column is a solution of silicic acids, polycondensation of which forms a sol with pH in the range of 1.3 to 3.0. To obtain sols with a different pH value, the resulting solutions are basified with suitable organic bases which will be further used for obtaining respective silicates with variations of the volume not exceeding 1%.

One known disadvantage of an ion exchange process for producing a silica sol is a limited residence time for the sodium silicate solution in the ion exchange apparatus due to low resistance of a sol to gelation. According to the invention, for avoiding clogging of the column with the gel fraction after removal of the sol with a pH of 2.3 to 3.0, passing of the sodium silicate solution (liquid glass) through the column is continued until the sol at the exit is obtained with pH 9. The ion exchange resin is flushed with a plenty of distilled water, and then a regeneration step is started. The obtained alkaline sol precursor solution is combined with liquid glass and can be used for recovering silica sol without alkaline metals.

In a direct ion-exchange synthesis, the range of concentrations of silica sol is defined as follows. The minimum concentration is determined solely from the economic and technological reasons. Thus, solutions with concentration of less than 3 mass % are too diluted, and their evaporation for obtaining concentrated solutions of silicates is associated with large expenditures.

According to the invention, the maximum achievable concentration of silica sol $SiO_2$, the obtaining of which does not require dismantling of the ion exchange column and washing of the resin with an alkali, should be in the range of 6 to 7 mass %. Thus, this concentration is an upper limit for direct ion-exchange synthesis of sols. Further increase of concentration is performed by evaporation or ultrafiltration of a stabilized sol.

Increase in the particle size from 2 to 7 nm improves stability of sols 8 to 10 times at all examined temperatures. Effect of concentration on the gel formation time showed that the time is proportional to the total surface of the particles, Thus, for diameter of particles d=5 nm an increase of the concentration from 3 to 5% at pH=5.5 leads to 9 to 10-fold drop in the stability of the system at temperatures in the range of 15 to 100° C.

It should be noted in this regard that in view of a very short life of sol it is not recommended to increase the sol concentration above 10 wt. % (100 g/l of $SiO_2$). It was established experimentally that the growth of the particles under the influence of temperature occurs mainly in the first 60 minutes. After that the rate of decrease in the specific surface is significantly reduced. Thus, the particle size is increased 2 to 2.5 times within 60 minutes and further only slightly modified.

Moreover, experimental data showed that the average size of colloidal particles in the sols obtained from liquid glass at all temperatures somewhat higher than in the case of sodium metasilicate. Probably, this is associated with a greater degree of polymerization in the silicon-oxygen frameworks of polysiloxane formations. This occurs because the silicate modulus of liquid glass is higher than that of the sodium metasilicate.

According to the invention, the most advantageous method for obtaining monodispersed silica sol with a predetermined particle size up to 150 nm is a synthesis method with a feeder. One of the important conditions for a steady increase in the particle size and decrease in polydispersity of the sol is the quality of the feeder and the speed of delivery from the feeder. It is not recommended to increase the particle size above 20 nm since this will reduce the rate of further reaction with an organic base.

Thus, according to the method of the invention, the silicon dioxide sol should be used with the particle size in the range of 2 to 20 nm and may have concentrations in the range of 1 to 100 g/l.

The silica sol obtained as described above is combined with a solution of a strong organic base. As a result, a finely divided silica-silica sol suspension is obtained. The obtained suspension is reacted with an aqueous solution of a strong organic base in a molar ratio of $SiO_2:M_2O$ (where M is an organic alkaline cation) in the range of 1.5 to 4.0.

It is possible to obtain products with a higher silicate modulus. However, in order to prevent premature coagulation it is necessary in this case to use sols with larger particles (see. FIG. 4).

Figure 5:
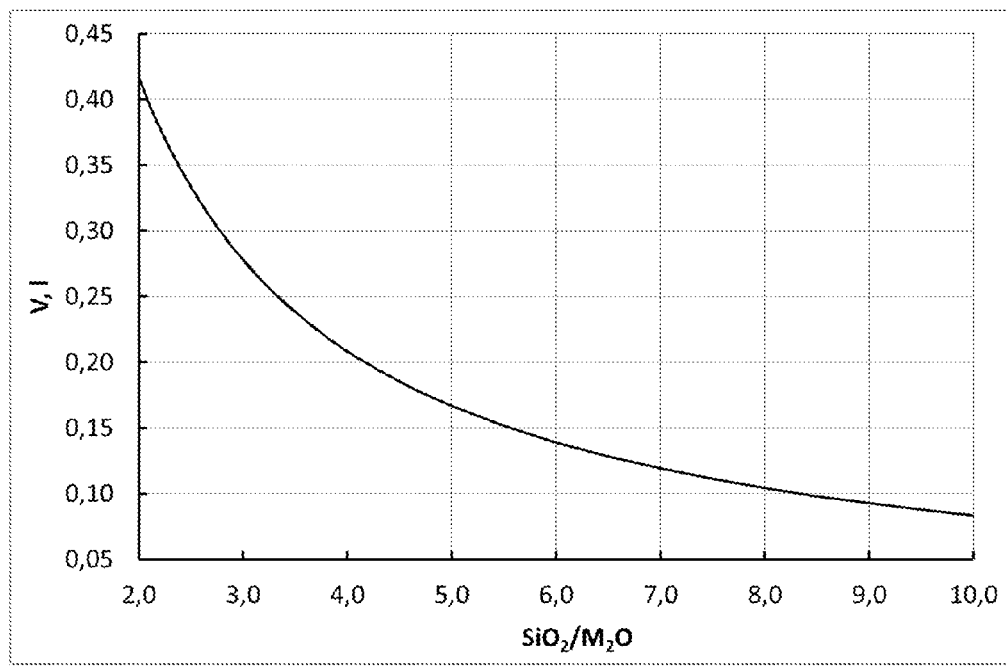
FIG. 5 shows volumes of the solution of a strong organic base with a concentration of 1.0 mol/l necessary for the interaction of 1 liter silica sol solution with a concentration of 5 wt % for obtaining the given silica modulus of the $SiO_2:M_2O$ ratio.

The graph of FIG. 5 shows the amount of the organic base solution which should be added in case of using a strong organic base solution with a concentration of 1 mol/l for achieving a desired silicate modulus. In fact, this graph is a nomogram for calculating the volume of the solution of a strong organic base with a concentration of 1 mol/l needed for obtaining a desired silica modulus $SiO_2:M_2O$ through interaction with 1 liter of a silica sol solution having concentration of 4.0 mass %.

In the case of solutions with different concentrations of the sol and the solution of a strong organic base, the amount of the added solution of a strong organic base is simply recalculated proportionally to the deviation of the sol concentration and strong organic base. Thus, from this graph it is seen that for 1.0 liter silica sol with a concentration of 5.0 wt. %, to achieve a silica modulus of $SiO_2:M_2O=3$, it is necessary to add 0.28 liters of a solution of a strong organic base with a concentration of 1.0 mol/l.

The silica sol obtained as described above having a concentration of 5 mass % and a particle size of 6.9 nm is combined with a solution of a strong organic base. The solution of a strong organic base is dosed in such a way as to achieve pH=9. Thus, for a 1.0 liter of a silica sol with a concentration of 5.0 mass %, to achieve pH=9 it is necessary to add 0.050 liter of a solution of a strong organic base with a concentration of 1.0 mol/l. The result of the process is a silicate solution of a strong organic base with a silicate modulus of $SiO_2:M_2O=16.4$.

In accordance with the method of the present invention, a strong organic base may comprise a hydroxide of quaternary ammonium bases of the following general formula:

$$R_1R_2R_3R_4NOH,$$

where $R_1$, $R_2$, $R_3$, $R_4$=$C_nH_m$—, n=1-5, m=3-13
with a molar ratio of $SiO_2:R_1R_2R_3R_4N_2O$ in the range of 1.5 to 4.0.

The amount of a solution of quaternary ammonium hydroxide to be added per 1.0 liter of silica sol at a concentration of 5 mass % needed to achieve, e.g., the silicate modulus of $M_2O:SiO_2=1:3$, should be equal to 0.14 liter of a solution of the organic quaternary ammonium base with concentration of 2 mol/l. After 1 hour retention, the resulting solution based on $SiO_2$ will have a concentration of 4.39 mass %.

In accordance with the method of the present invention, a strong organic base may comprise a hydroxide of 1,5-diazabicyclo [4.3.0] non-5-ene (hereinafter DBN) or 1,8-diazabicyclo [5.4.0] undec-7-ene (hereinafter DBU) in molar ratio of $SiO_2:M_2O$ from 1.5 to 4.0 (where M=$C_7H_{13}N_2$ or $C_9H_{17}N_2$). The amount of (DBN) or (DBU), e.g., for 1.0 liter of silica sol with a concentration of 10 wt. %, needed for obtaining a silica modulus $SiO_2:M_2O=3.1$, should be 0.269 liter for DBN or DBU at concentration of 2 mol/l. After 1 hour retention, the resulting solution based on $SiO_2$ will acquire a concentration of 7.88 mass %.

Alternatively, in accordance with the method of the present invention, a strong organic base may comprise a hydroxide of piperidine and its derivatives, 4-dimethylaminopyridine, or diisopropylethylamine (Hünig's base) in a molar ratio of $SiO_2:M_2O$ from 1.5 to 4.0 (where M=piperidinium, 4-dimethylaminopyridinium, or diizopropyl-ethylammonium (cation of the Hunig's base)). For example, the amount of hydroxide of piperidine, 4-dimethyl aminopyridine, or diisopropyl ethylamine (Hünig's base) with concentration of 2 mole/liter should be added per 1 liter of the silicon sol with concentration of 10 mass % for obtaining the silicate modulus of $SiO_2:M_2O=2.8$, is 0.298 liter.

After 1 hour retention, the resulting solution based on $SiO_2$ will have a concentration of 7.70 mass %.

In accordance with another aspect of the invention, a strong organic base may comprise a hydroxide of 1,8-bis (dimethylamino) naphthalene, 2,7-dimethoxy-1,8-bis (dimethylamino) naphthalene, or 2,7-dimethylamino 1,8-bis (dimethylamino) naphthalene in a molar ratio of $SiO_2:M_2O$ from 1.5 to 3.5 (where M=1,8-bis (dimethylamino) naphthalene, 2,7-dimethoxy-1,8-bis (dimetilamino) naphthalene, or 2,7-dimethylamino 1 8-bis (dimetilamino) naphthalene).

For example, the amount of hydroxide of 1,8-bis (dimethylamino) naphthalene, 2,7-dimethoxy-1,8-bis (dimethylamino) naphthalene, or 2,7-dimethylamino 1,8-bis (dimethylamino) naphthalene with concentration of 2.0 mole/liter which should be added per 1 liter of the silicon sol with concentration of 10 mass % for obtaining the silicate modulus of $SiO_2:M_2O=3.3$, is 0.253 liter. After 1 hour retention, the resulting solution based on $SiO_2$ will have a concentration of 7.98 mass %.

In accordance with another aspect of the invention, a strong organic base may comprise a hydroxide of guanidine or hydroxide base derivatives in a molar ratio of $SiO_2:M_2O$ from 1.5 to 4.0 (where M is guanidine or hydroxide base derivatives For example, the amount of hydroxide of guanidine or hydroxide base derivatives with concentration of 2 mole/liter which should be added per 1 liter of the silicon sol with concentration of 10 mass % for obtaining the silicate modulus of $SiO_2:M_2O=3.4$, is 0.245 liter. After 1 hour retention, the resulting solution based on $SiO_2$ will have a concentration of 8.03 mass %.

If it is necessary to obtain a silicate solution of an organic base having higher concentrations, then the solution obtained after synthesis is evaporated under vacuum with the use of rotational or rotary evaporators.

To prevent destructive processes in silicates with organic bases, evaporation is carried out at a temperature of 20 to 30° C. and a pressure less than 2.3 kPa. Raising the temperature above 30° C. increases probability of destructive processes in the silicate solutions of strong organic bases. Lowering the temperature below 20° C. and increasing the pressure above 4.2 kPa lead to an increase in the duration of the evaporation process, which is disadvantageous from the economic and technological point of views. Pressure reduced below 2.3 kPa, requires the use of special vacuum technique, which is also not justifiable from the economic and technological points of view.

To obtain a product in the form of a power, the silicate solution of an organic base should be subjected to spray drying. For this purpose, the evaporated solution is sprayed with a spray drier. The resulting material can be re-dissolved in water.

PRACTICAL EXAMPLES

Hereinafter, the invention will be described in more detail by of practical examples. It is understood that these examples should not be construed as limiting the invention.

Practical Examples 1

A liquid glass solution with a content of $SiO_2$ in the range of 3 to 6% was passed through a bed of cation exchanger in the H form. In the process of the exchange the sodium ions remain in the resin, and as a result, the column produced on its outlet a solution of silicic acids, polycondensation of which could produce a sol with pH in the range of 2.3 to 3.0. To obtain sols with different pH values, the resulting solutions were basified with solutions of organic bases, silicates of which could be obtained later, and so that the total volume change would not exceed 1%.

The resulting alkaline sol was combined with the initial liquid glass solution to be used later for recovery of silica sol without alkaline metals.

The maximum achievable concentration of silica sol that can be obtained without need in subsequent dismantling of the ion exchange column and washing of the resin with an alkali was 6 to 7 mass % of $SiO_2$.

Further increase in concentration of the sol was achieved by evaporation or ultrafiltration. In general, the water content of the organic alkali silicates may vary from zero to 100% without loss of homogeneity. However, depending on the silica modulus and types of organic bases, concentrations more or less acceptable for the stability of the system obtained by evaporation or ultrafiltration should be in the range of 30 to 35 mass % $SiO_2$. Products with higher concentrations practically impossible to remove from the reaction vessel due to their high viscosity, or short lifetime in the case of high modulus systems. Further concentration can be achieved only by evaporation, and only in cases of obtaining dry products. Thus, depending on the type and quantity of an organic base silicate modulus of $SiO_2:M_2O$, the content of $SiO_2$, in the resulting products may have a value in the range of 55 to 65 mass %.

Practical Example 2

The silica sol obtained in Practical Example 1 and having a concentration of 5 mass % was combined with a solution of a strong organic base such as hydroxide of tetraethylammonium. As a result, a suspension of finely divided silica/silica sol was obtained. The resulting suspension of finely divided silica/silica sol was reacted with an aqueous solution of a strong organic base in a molar ratio of $SiO_2:M_2O$ in the range of 1.5 to 4.0 (where M was an organic alkaline cation of ammonium hydroxide). It was possible to obtain products with a higher silicate modulus, but for this purpose in order to prevent premature coagulation it was necessary to use sols with particles of a larger size (see. FIG. 3).

In the case of a strong organic base solution of tetraethyl ammonium hydroxide with a concentration of 1.0 mol/l, the amount of the organic base solution which should be added for achieving the desired silica modulus is shown in FIG. 4. Thus, as follows from the test conducted in this example, to achieve silica modulus of $SiO_2:M_2O=3$, it is necessary to add to a 1.0 liter of silica sol with a concentration of 5.0 mass % a solution of a strong organic base with the concentration of 1 mol/l in an amount of 0.28 liters.

Practical Example 3

The silica sol obtained in Practical Example 1 at a concentration of 5 wt. % and with the particle size of 6.9 nm was combined with a solution of a strong organic base such as tetraethylammonium hydroxide. A solution of tetraethylammonium hydroxide was added in dosed quantities in such a way as to achieve pH=9. Thus, to achieve pH=9, the solution of the tetraethylammonium hydroxide with a concentration of 1.0 mol/l should be added in an amount of 0.050 liter per 1 liter of silica sol with a concentration of 5.0 mass %. In this process, a silicate solution of the tetraethylammonium hydroxide with a silicate modulus of $SiO_2:M_2O=16.4$ was obtained.

Practical Example 4

The silica sol obtained in Example 1 at a concentration of 5.0 mass % was combined with a solution of a strong organic base. In this case, a quaternary ammonium hydroxide base of the following general formula:

$R_1R_2R_3R_4NOH$, where 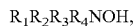 $R_1$, $R_2$, $R_3$, $R_4$=n=1-5, m=3-13 at a molar ratio of $SiO_2:R_1R_2R_3R_4N_2O$ in the range of 1.5 to 3.5, was used as an organic alkali. To achieve a silicate modulus of $M_2O:SiO_2$ in the range of 1 to 3, it is necessary to add 0.14 liter of the strong organic base solution with concentration of 2.0 moles per 1.0 liter of silica sol with concentration of 5.0 mass %. After retention for 1 hour, the resulting solution had in terms of $SiO_2$ the concentration of 4.39 mass %.

Practical Example 5

The silica sol obtained in Practical Example 1 at a concentration of 10 mass % was combined with a solution of a strong organic base. In this case, the used organic alkali comprised a hydroxide of 1,5-diazabicyclo [4.3.0] non-5-ene (DBN) or 1,8-diazabicyclo-[5.4.0] undec-7-ene (DBU) in a molar ratio of $SiO_2:M_2O$ in the range of 1.5 to 3.5 (where $M=C_7H_{13}N_2$ or $C_9H_{17}N_2$). To achieve the silicate modulus of $SiO_2:M_2O=3.1$, the solution of 1,5-diazabicyclo [4.3.0] non-5-ene (DBN) or 1,8-diazabicyclo-[5.4.0] undec-7-ene (DBU) should be added in the amount of 0.269 liter at concentration of 2.0 moles per 1.0 liter of silica sol at concentration of 10 mass %. After retention for 1 hour, the resulting solution had in terms of $SiO_2$ the concentration of 7.88 mass %.

Practical Example 6

The silica sol obtained in Practical Example 1 at a concentration of 10 mass % was combined with a solution of a strong organic base. In this case, the used organic alkali comprised a hydroxide of piperidine or its derivatives, 4-dimethylaminopyridine, or diisopropylethylamine (Hünig's base) in a molar ratio of $SiO_2:M_2O$ in the range of 1.5 to 3.5 (where M is piperidin-1-ium, 4-dimethylaminopyridine or diisopropylethylamine (cation of the Hünig's base).

To achieve the silicate modulus of $SiO_2:M_2O=2.8$, the solution of hydroxide of piperidine or its derivatives, 4-dimethylaminopyridine, or diisopropylethylamine (Hünig's base) should be added in the amount of 0.298 liter at concentration of 2.0 moles per 1.0 liter of silica sol at concentration of 10 mass %. After retention for 1 hour, the resulting solution had in terms of $SiO_2$ the concentration of 7.88 mass %.

Practical Example 7

The silica sol obtained in Practical Example 1 at a concentration of 10 mass % was combined with a solution of a strong organic base. In this case, the used organic alkali comprised hydroxide of 1,8-bis (dimethylamino) naphthalene, 2,7-dimethoxy-1,8-bis (dimethylamino) naphthalene, or 2,7-dimethylamino 1,8-bis (dimethylamino) naphthalene in a molar ratio of $SiO_2:M_2O$ in the range of 1.5 to 3.5 (where M=1,8-bis (dimetilamino) naphthalene, 2,7-dimethoxy 1 8-bis (dimetilamino) naphthalene, or 2,7-dimethylamino-1,8 bis (dimethylamino) naphthalene). To achieve the silicate modulus of $SiO_2:M_2O=3.3$, the hydroxide of 1,8-bis (dimethylamino) naphthalene, 2,7-dimethoxy-1,8-bis (dimethylamino) naphthalene, or 2,7-dimethylamino 1,8-bis (dimethylamino) naphthalene at concentration of 2.0 mol/liter should be added in the amount of 0.253 liter per 1.0 liter of silica sol with a concentration of 10 mass %. After retention for 1 hour, the resulting solution had in terms of $SiO_2$ the concentration of 7.98 mass %.

Practical Example 8

The silica sol obtained in Practical Example 1 at a concentration of 10 mass % was combined with a solution of a strong organic base. In this case, the used organic alkali comprised hydroxide of guanidine or derivatives of guanidine bases in a molar ratio of $SiO_2:M_2O$ in the range of 1.5 to 4.0 (where M=guanidinium or a cation of guanidinium base derivatives). To achieve silica modulus of $SiO_2:M_2O=3.4$, the solution of hydroxide of guanidine or derivatives of guanidine bases at concentration of 2.0 mol/liter should be added in the amount of 0.245 liter per 1.0 liter of silica sol at concentration of 10 mass %. After retention for 1 hour, the resulting solution had in terms of $SiO_2$ the concentration of 8.03 mass %.

Practical Example 9

To further increase concentration of the solution, the organic base silicate solution obtained in Example 3 was evaporated under vacuum. Evaporation was carried out with the use of vacuum rotary or rotor evaporators. To prevent destructive processes in silicates of organic bases, evaporation was carried out at a temperature in the range of 20 to 30° C. and under a pressure less than 4.2 kPa.

Practical Example 10

To obtain a product in the form of a power, the silicate solution of an organic base was subjected to spray drying. For this purpose, the evaporated solution obtained in Practical Example 9 was sprayed with a spray drier. The resulting material can be re-dissolved in water.

What is claimed is:

1. A method of producing soluble silicates with organic cations at a given silicate modulus in the range of 1.5 to 20, the method comprising the steps of:
    providing an aqueous suspension of a silica sol with silica particle size in the range of 2 to 20 nm;
    providing an aqueous solution of a strong organic base with a constant of base dissociation $pK_b$ equal to or greater than 4;
    reacting the liquid suspension of a silica with the aqueous solution of a strong organic base thus obtaining a solution of soluble silicates with organic cations at a silicate modulus in the range of 1.5 to 20.

2. The method of claim 1, wherein the given silicate modulus is a molar ratio of $SiO_2:M_2O$, wherein M is an organic alkali cation.

3. The method of claim 2, wherein a strong organic base with a constant of base is selected from hydroxides of said strong organic bases.

4. The method of claim 3, wherein the hydroxides of the strong organic bases are selected from the group consisting of:
    (a) hydroxide of a quaternary ammonium base represented by the following general formula: $R_1R_2R_3R_4NOH$, where $R_1$, $R_2$, $R_3$, $R_4=C_nH_m-$, n=1-5, and m=3-13;
    (b) hydroxide of 1,8-diazabicycloundecene-7;
    (c) hydroxide of 1,5-diazabicyclononene-5;
    (d) hydroxide of 1,8-bis (dimethylamino) naphthalene;
    (e) hydroxide of 2,7-dimethoxy-1,8-bis (dimethylamino) naphthalene;
    (f) hydroxide of 2,7-dimethylamino 1,8-bis (dimethylamino) naphthalene;
    (g) hydroxide of piperidine;
    (h) hydroxide of piperidine derivatives;
    (i) hydroxide of 4-dimethylaminopyridine;
    (j) hydroxide of diisopropylethylamine;
    (k) hydroxide of guanidine bases and their derivatives;
    (l) hydroxide 1,5-diazabicyclo [4.3.0] non-5-ene (DBN); and
    (m) hydroxide 1,8-diazabicyclo [5.4.0] undec-7-ene (DBU).

5. The method according to claim 1, wherein the silica sol is obtained by providing solutions of alkali metal silicates that contain alkali metals; and removing alkaline metals from solutions of alkali metal silicates by an ion exchange process.

6. The method of claim 5, wherein a strong organic base with a constant of base is selected from hydroxides of said strong organic bases.

7. The method of claim 6, wherein the hydroxides of the strong organic bases are selected from the group consisting of:
    (a) hydroxide of a quaternary ammonium base represented by the following general formula: $R_1R_2R_3R_4NOH$, where $R_1$, $R_2$, $R_3$, $R_4=C_nH_m-$, n=1-5, and m=3-13;
    (b) hydroxide of 1,8-diazabicycloundecene-7;
    (c) hydroxide of 1,5-diazabicyclononene-5;
    (d) hydroxide of 1,8-bis (dimethylamino) naphthalene;
    (e) hydroxide of 2,7-dimethoxy-1,8-bis (dimethylamino) naphthalene;
    (f) hydroxide of 2,7-dimethylamino 1,8-bis (dimethylamino) naphthalene;
    (g) hydroxide of piperidine;
    (h) hydroxide of piperidine derivatives;
    (i) hydroxide of 4-dimethylaminopyridine;
    (j) hydroxide of diisopropylethylamine;
    (k) hydroxide of guanidine bases and their derivatives;
    (l) hydroxide 1,5-diazabicyclo [4.3.0] non-5-ene; and
    (m) hydroxide 1,8-diazabicyclo [5.4.0] undec-7-ene.

8. The method of claim 1, wherein the silica particles have a size in the range of 2 to 20 nm.

9. The method of claim 8, wherein the given silicate modulus is a molar ratio of $SiO_2:M_2O$, wherein M is an organic alkali cation.

10. The method of claim 9, wherein a strong organic base with a constant of base is selected from hydroxides of said strong organic bases.

11. The method of claim 10, wherein the hydroxides of the strong organic bases are selected from the group consisting of:
    (a) hydroxide of a quaternary ammonium base represented by the following general formula: $R_1R_2R_3R_4NOH$, where $R_1$, $R_2$, $R_3$, $R_4=C_nH_m-$, n=1-5, and m=3-13;
    (b) hydroxide of 1,8-diazabicycloundecene-7;
    (c) hydroxide of 1,5-diazabicyclononene-5;
    (d) hydroxide of 1,8-bis (dimethylamino) naphthalene;
    (e) hydroxide of 2,7-dimethoxy-1,8-bis (dimethylamino) naphthalene;
    (f) hydroxide of 2,7-dimethylamino 1,8-bis (dimethylamino) naphthalene;
    (g) hydroxide of piperidine;
    (h) hydroxide of piperidine derivatives;
    (i) hydroxide of 4-dimethylaminopyridine;
    (j) hydroxide of diisopropylethylamine; and
    (k) hydroxide of guanidine bases and their derivatives;
    (l) hydroxide 1,5-diazabicyclo [4.3.0] non-5-ene; and
    (m) hydroxide 1,8-diazabicyclo [5.4.0] undec-7-ene.

12. The method according to claim 1, wherein the silica sol is obtained by providing solutions of alkali metal silicates that contains alkali metals; and removing alkaline metals from solutions of alkali metal silicates by an ion exchange process.

13. The method of claim 12, wherein a strong organic base with a constant of base is selected from hydroxides of said strong organic bases.

14. The method of claim 13, wherein the hydroxides of the strong organic bases are selected from the group consisting of:
    (a) hydroxide of a quaternary ammonium base represented by the following general formula: $R_1R_2R_3R_4NOH$, where $R_1$, $R_2$, $R_3$, $R_4=C_nH_m-$, n=1-5, and m=3-13;
    (b) hydroxide of 1,8-diazabicycloundecene-7;
    (c) hydroxide of 1,5-diazabicyclononene-5;
    (d) hydroxide of 1,8-bis (dimethylamino) naphthalene;
    (e) hydroxide of 2,7-dimethoxy-1,8-bis (dimethylamino) naphthalene;

(f) hydroxide of 2,7-dimethylamino 1,8-bis (dimethylamino) naphthalene;
(g) hydroxide of piperidine;
(h) hydroxide of piperidine derivatives;
(i) hydroxide of 4-dimethylaminopyridine;
(j) hydroxide of diisopropylethylamine; and
(k) hydroxide of guanidine bases and their derivatives;
(l) hydroxide 1,5-diazabicyclo [4.3.0] non-5-ene;
(m) hydroxide 1,8-diazabicyclo [5.4.0] undec-7-ene.

15. The method of claim 1, wherein the silica sol is used with concentration of silica in silica sol in the range of 1 to 100 g/l.

16. The method of claim 14, wherein the silica sol is used with concentration of silica in silica sol in the range of 1 to 100 g/l.

17. The method of claim 1, wherein the soluble silicates with organic cations is obtained in a powdered form by evaporating the solution of the soluble silicates under vacuum below 4.2 kPa and at a temperature in the range of 20 to 30° C. thus obtaining a product of evaporation, and then drying the product of evaporation by spraying.

18. The method of claim 14, wherein the soluble silicates with organic cations is obtained in a powdered form by evaporating the solution of the soluble silicates under vacuum below 4.2 kPa and at a temperature in the range of 20 to 30° C. thus obtaining a product of evaporation, and then drying the product of evaporation by spraying.

19. The method of claim 1, wherein the given silicate modulus, which is a molar ratio of $SiO_2:M_2O$, wherein M is a organic alkali cation, is obtained by plotting a curve on graph that shows dependence of the molar ratio of $SiO_2:M_2O$ from the volume of the solution of the strong organic base with a concentration of 1.0 mol/l necessary for the interaction of 1.0 liter silica sol with a concentration of 5 wt % for obtaining the given silica modulus of the $SiO_2:M_2O$ ratio.

20. The method of claim 14, wherein the given silicate modulus, which is a molar ratio of $SiO_2:M_2O$, wherein M is a organic alkali cation, is obtained by plotting a curve on graph that shows dependence of the molar ratio of $SiO_2:M_2O$ from the volume of the solution of the strong organic base with a concentration of 1.0 mol/l necessary for the interaction of 1.0 liter silica sol with a concentration of 5 wt % for obtaining the given silica modulus of the $SiO_2:M_2O$ ratio.

21. The method of claim 18, wherein the soluble silicates with organic cations are obtained in a powdered form by evaporating the solution of the soluble silicates under vacuum below 4.2 kPa and at a temperature in the range of 20 to 30° C. thus obtaining a product of evaporation, and then drying the product of evaporation by spraying.

* * * * *